United States Patent
Dubreuil et al.

(10) Patent No.: US 12,168,221 B2
(45) Date of Patent: Dec. 17, 2024

(54) CATALYST COMPRISING AN ACTIVE NICKEL PHASE IN THE FORM OF SMALL PARTICLES AND A NICKEL-COPPER ALLOY

(71) Applicant: IFP Energies Nouvelles, Rueil-Malmaison (FR)

(72) Inventors: Anne-Claire Dubreuil, Rueil-Malmaison (FR); Malika Boualleg, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 424 days.

(21) Appl. No.: 17/630,238

(22) PCT Filed: Jul. 16, 2020

(86) PCT No.: PCT/EP2020/070077
§ 371 (c)(1),
(2) Date: Jan. 26, 2022

(87) PCT Pub. No.: WO2021/018599
PCT Pub. Date: Feb. 4, 2021

(65) Prior Publication Data
US 2022/0280922 A1    Sep. 8, 2022

(30) Foreign Application Priority Data
Jul. 31, 2019  (FR) ...................................... 1908725

(51) Int. Cl.
| | |
|---|---|
| *B01J 23/755* | (2006.01) |
| *B01J 21/04* | (2006.01) |
| *B01J 35/23* | (2024.01) |
| *B01J 35/30* | (2024.01) |
| *B01J 35/40* | (2024.01) |
| *B01J 37/02* | (2006.01) |
| *B01J 37/16* | (2006.01) |
| *C07C 5/09* | (2006.01) |
| *C07C 5/10* | (2006.01) |

(52) U.S. Cl.
CPC .......... *B01J 23/755* (2013.01); *B01J 21/04* (2013.01); *B01J 35/23* (2024.01); *B01J 35/393* (2024.01); *B01J 35/40* (2024.01); *B01J 37/0219* (2013.01); *B01J 37/0228* (2013.01); *B01J 37/0236* (2013.01); *B01J 37/16* (2013.01); *C07C 5/09* (2013.01); *C07C 5/10* (2013.01); *C07C 2521/04* (2013.01); *C07C 2523/72* (2013.01); *C07C 2523/755* (2013.01)

(58) Field of Classification Search
CPC . B01J 23/755; B01J 21/04; B01J 35/23; B01J 35/393; B01J 35/40; B01J 37/0219; B01J 37/0228; B01J 37/0236; B01J 37/16; C07C 5/09; C07C 5/10; C07C 2521/04; C07C 2523/72; C07C 2523/755; C07C 5/03
USPC ........................................................ 585/262
See application file for complete search history.

(56) References Cited

U.S. PATENT DOCUMENTS

| | | | |
|---|---|---|---|
| 5,208,405 | A | 5/1993 | Cheung et al. |
| 5,948,942 | A | 9/1999 | Ramirez de Agudelo et al. |
| 8,586,808 | B2 | 11/2013 | Dubreuil et al. |
| 8,637,425 | B2 | 1/2014 | Fischer et al. |
| 9,783,745 | B2 | 10/2017 | Corvaisier et al. |
| 2004/0192966 | A1* | 9/2004 | Hazin ................... C07C 51/215 502/312 |
| 2011/0160503 | A1 | 6/2011 | Fischer et al. |
| 2016/0264882 | A1* | 9/2016 | Corvaisier ............. C10G 45/36 |
| 2021/0154654 | A1 | 5/2021 | Boualleg et al. |

FOREIGN PATENT DOCUMENTS

| | | |
|---|---|---|
| FR | 2927267 B1 | 4/2010 |
| FR | 3064500 A1 | 10/2018 |
| FR | 3076746 A1 | 7/2019 |
| WO | 2019201617 A1 | 10/2019 |

OTHER PUBLICATIONS

Min Kang et al: "[gamma]-Alumina supported Cu-Ni bimetallic catalysts: Characterization and selective hydrogenation of 1,3-butadiene", Canadian Journal of Chemical Engineering, vol. 80, No. 1, Feb. 2002 (Feb. 1, 2002), pp. 63-70, XP055672478.
International Search report PCT/EP2020/070077 dated Sep. 2, 2020 (pp. 1-3).

* cited by examiner

*Primary Examiner* — Prem C Singh
*Assistant Examiner* — Francis C Campanell
(74) *Attorney, Agent, or Firm* — Millen, White, Zelano & Branigan; Csaba Henter

(57) ABSTRACT

Catalyst comprising nickel and copper, in a proportion of 1% to 50% by weight of nickel element relative to the total weight of the catalyst, in a proportion of 0.5% to 15% by weight of copper element relative to the total weight of the catalyst, and an alumina support, said catalyst being characterized in that:
 the mole ratio between nickel and copper is between 0.5 and 5 mol/mol;
 at least one portion of the nickel and copper is in the form of a nickel-copper alloy;
 the nickel content in the nickel-copper alloy is between 0.5% and 15% by weight of nickel element relative to the total weight of the catalyst,
 the size of the nickel particles in the catalyst is less than 7 nm.

13 Claims, No Drawings

CATALYST COMPRISING AN ACTIVE NICKEL PHASE IN THE FORM OF SMALL PARTICLES AND A NICKEL-COPPER ALLOY

TECHNICAL FIELD

The present invention relates to a supported metal catalyst based on nickel and copper intended particularly for the hydrogenation of unsaturated hydrocarbons, and more particularly for the selective hydrogenation of polyunsaturated compounds or the hydrogenation of aromatics.

PRIOR ART

The catalysts for the hydrogenation of aromatic compounds are generally based on metals from Group VIII of the Periodic Table of the Elements, such as nickel. The metal is in the form of nanoscale metal particles deposited on a support which may be a refractory oxide. The content of metal from Group VIII, the optional presence of a second metal element, the size of the metal particles and the distribution of the active phase in the support and also the nature and the pore distribution of the support are parameters which may have an influence on the performance of the catalysts.

The rate of the hydrogenation reaction is governed by several criteria, such as the diffusion of the reactants toward the surface of the catalyst (external diffusional limitations), the diffusion of the reactants in the porosity of the support toward the active sites (internal diffusional limitations) and the intrinsic properties of the active phase, such as the size of the metal particles and the distribution of the active phase within the support.

The promotion of a nickel-based catalyst has frequently been proposed in order to improve performance levels in hydrogenation of unsaturated hydrocarbons. By way of illustration, U.S. Pat. No. 5,208,405 discloses a catalyst based on nickel and silver for the selective hydrogenation of C4-C10 diolefins. Furthermore, it is known to promote nickel, predominantly present, with metals of group IB, in particular gold (FR 2 949 077) or tin (FR 2 949 078). Document FR 3 011 844 discloses a catalyst for the implementation of a selective hydrogenation process comprising a support and an active metallic phase deposited on the support, the active metallic phase comprising copper and at least one nickel or cobalt metal in a Cu:(Ni and/or Co) mole ratio greater than 1.

Moreover, prior to the employment of such catalysts and the use thereof in a hydrogenation process, a step of reducing treatment in the presence of a reducing gas is carried out so as to obtain a catalyst comprising an active phase at least partially in metallic form. This treatment makes it possible to activate the catalyst and to form metallic particles. This treatment may be carried out in situ or ex situ, that is to say after or before the catalyst is charged to the hydrogenation reactor.

Lastly, with a view to obtaining better catalytic performance, in particular a better selectivity and/or activity, it is known in the prior art to use additives of organic compound type for the preparation of metallic catalysts for the selective hydrogenation or hydrogenation of aromatics.

OBJECTS OF THE INVENTION

Continuing its research in the field of hydrogenating catalysts, the applicant has now discovered that it is possible to prepare catalysts which are particularly active, and particularly selective, in the selective hydrogenation of polyunsaturated compounds or in the hydrogenation of aromatic compounds, by bringing into contact on a porous support, in a specific order, at least one nickel precursor, at least one copper precursor, and at least one specific organic compound, with a specific Cu:Ni ratio, and by carrying out, after these contacting steps, a step of reduction in the catalytic reactor in the presence of a reducing gas, at a temperature below 200° C. Without wishing to be bound by any theory, it has been observed by the applicant that, during the preparation of the catalyst, the presence of copper greatly improves the reducibility of the nickel on the support which makes it possible to carry out a step of reducing the metal elements in the presence of a reducing gas at lower temperatures and shorter reaction times than those commonly used in the prior art. The use of less severe operating conditions than in the prior art makes it possible to directly carry out the reduction step within the reactor in which it is desired to carry out the hydrogenation of the unsaturated compounds or the aromatic compounds.

Moreover, it has been observed by the applicant that, during the preparation of the catalyst, carrying out a step of bringing the support into contact with at least one solution simultaneously containing a copper-based metal precursor and a nickel-based metal precursor, followed by a step of final drying and reducing in the presence of a reducing gas at low temperature (between 150° C. and 250° C.) makes it possible to obtain a nickel-copper alloy (in reduced form) which unexpectedly makes it possible to greatly improve the reducibility of the nickel active phase on the support. Furthermore, the presence of copper in the catalyst makes it possible to maintain good activity and a longer service life of the catalyst when the latter is placed in contact with a hydrocarbon feedstock comprising sulfur, notably in aromatic hydrocarbon fractions. Indeed, compared to nickel, the copper present in the catalyst more easily captures the sulfur-containing compounds included in the feedstock, which limits the irreversible poisoning of the active sites.

It has further been observed that the catalysts according to the invention prepared in the presence of an organic compound (cited below) are much more active than the catalysts prepared in the absence of this type of organic compound.

The relative synergistic effect obtained in this preparation process makes it possible to obtain a catalyst comprising nickel which has a small particle size, is particularly active, reducible at low temperature and particularly selective, in selective hydrogenation of polyunsaturated compounds or in hydrogenation of aromatic compounds.

A first subject according to the invention relates to a catalyst comprising nickel and copper, in a proportion of 1% to 50% by weight of nickel element relative to the total weight of the catalyst, in a proportion of 0.5% to 15% by weight of copper element relative to the total weight of the catalyst, and an alumina support, said catalyst being characterized in that:
- the mole ratio between nickel and copper is between 0.5 and 5 mol/mol;
- at least one portion of the nickel and copper is in the form of a nickel-copper alloy;
- the nickel content in the nickel-copper alloy is between 0.5% and 15% by weight of nickel element relative to the total weight of the catalyst,
- the size of the nickel particles in the catalyst is less than 7 nm.

Advantageously, the size of the nickel particles in the catalyst is less than 5 nm.

Advantageously, the support is in the form of an extrudate with a mean diameter of between 0.5 and 10 mm.

Advantageously, the support is in the form of a trilobate or quadrilobate extrudate.

Another subject according to the invention relates to a process for preparing a catalyst according to the invention, comprising the following steps:

a) the alumina support is brought into contact with at least one solution containing at least one nickel precursor;

b) the alumina support is brought into contact with at least one solution containing at least one nickel precursor and at least one copper precursor;

c) the alumina support is brought into contact with at least one solution containing at least one organic compound comprising at least one carboxylic acid function, or at least one alcohol function, or at least one ester function, or at least one amide function, or at least one amine function, it being understood that:

steps a), b) and c) are carried out separately, in any order, or steps a) and c) are carried out at the same time, step b) being carried out either before the combination of steps a) and c), or afterwards;

steps b) and c) are carried out at the same time, step a) being carried out either before the combination of steps b) and c), or afterwards;

d) at least one step of drying the catalyst precursor obtained at the end of steps a) to c) is carried out at a temperature below 250° C.;

e) a step of reducing the catalyst precursor obtained at the end of step d) is carried out by bringing said precursor into contact with a reducing gas at a temperature above or equal to 150° C. and below 250° C.

Advantageously, the mole ratio between said organic compound introduced in step c) and the nickel element also introduced in step a) is between 0.01 and 5.0 mol/mol.

Advantageously, the organic compound of step c) is chosen from oxalic acid, malonic acid, glycolic acid, lactic acid, tartronic acid, citric acid, tartaric acid, pyruvic acid, levulinic acid, ethylene glycol, propane-1,3-diol, butane-1,4-diol, glycerol, xylitol, mannitol, sorbitol, glycol, glucose, dimethyl carbonate, diethyl carbonate, formamide, N-methylformamide, acetamide, N-methylacetamide, N,N-dimethylmethanamide, 2-pyrrolidone, γ-lactam, lactamide, urea, alanine, arginine, lysine, proline, serine, EDTA.

Advantageously, step e) is carried out at a temperature between 130° C. and 190° C.

Advantageously, step e) is carried out for between 10 minutes and 110 minutes.

Advantageously, the copper content is between 0.5% and 12% by weight of copper element relative to the total weight of the catalyst.

Advantageously, the copper precursor is chosen from copper acetate, copper acetylacetonate, copper nitrate, copper sulfate, copper chloride, copper bromide, copper iodide or copper fluoride. Preferably, the copper precursor is copper nitrate.

Another subject according to the invention relates to a process for the selective hydrogenation of polyunsaturated compounds containing at least 2 carbon atoms per molecule, contained in a hydrocarbon feedstock having a final boiling point below or equal to 300° C., said process being carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^-$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of a catalyst according to the invention.

Another subject according to the invention relates to a process for the hydrogenation of at least one aromatic or polyaromatic compound contained in a hydrocarbon feedstock having a final boiling point below or equal to 650° C., said process being carried out in the gas phase or in the liquid phase, at a temperature of between 30° C. and 350° C., at a pressure of between 0.1 and 20 MPa, at a hydrogen/(aromatic compounds to be hydrogenated) mole ratio of between 0.1 and 10 and at an hourly space velocity HSV of between 0.05 and 50 $h^-$, in the presence of a catalyst according to the invention.

DETAILED DESCRIPTION OF THE INVENTION

1. Definitions

In the text hereinbelow, the groups of chemical elements are given according to the CAS classification (CRC Handbook of Chemistry and Physics, published by CRC Press, editor-in-chief D. R. Lide, 81st edition, 2000-2001). For example, group VIII according to the CAS classification corresponds to the metals of columns 8, 9 and 10 according to the new IUPAC classification.

The degree of reduction (DR) of a metal M contained in the catalyst is defined as being the percentage of said metal M reduced after the step of reducing said catalyst. The degree of reduction (DR) corresponds to the ratio between the amount of metal reduced (M1) and the amount of theoretically reducible metal present on the catalyst, measured by X-ray fluorescence (M2), i.e. DR (%)=(M1/M2)× 100. In the context of the present invention, the degree of reduction of the nickel (Ni) was measured by X-ray diffraction (XRD) analysis. The description of the method for measuring the amount of reducible metal on oxide catalysts is explained later in the description (cf. examples section).

The expression "the specific surface area" of the catalyst or of the support used for the preparation of the catalyst according to the invention is intended to mean the BET specific surface area determined by nitrogen adsorption in accordance with standard ASTM D 3663-78 drawn up from the Brunauer-Emmett-Teller method described in the journal "The Journal of the American Chemical Society", 60, 309 (1938).

In the present application, the term "to comprise" is synonymous with (means the same thing as) "to include" and "to contain", and is inclusive or open and does not exclude other elements not stated. It is understood that the term "to comprise" includes the exclusive and closed term "to consist of".

The term "macropores" is intended to mean pores, the opening of which is greater than 50 nm.

The term "mesopores" is intended to mean pores, the opening of which is between 2 nm and 50 nm, limits included.

The term "micropores" is intended to mean pores, the opening of which is less than 2 nm.

The term "total pore volume" of the catalyst or of the support used for the preparation of the catalyst according to the invention is intended to mean the volume measured by intrusion with a mercury porosimeter according to standard ASTM D4284-83 at a maximum pressure of 4000 bar (400 MPa), using a surface tension of 484 dyne/cm and a contact angle of 140°. The wetting angle was taken equal to 140° following the recommendations of the work "Techniques de l'ingénieur, traité analyse et caractérisation" [Techniques of the Engineer, Analysis and Characterization Treatise], pages 1050-1055, written by Jean Charpin and Bernard Rasneur.

In order to obtain better accuracy, the value of the total pore volume corresponds to the value of the total pore volume measured by intrusion with a mercury porosimeter measured on the sample minus the value of the total pore volume measured by intrusion with a mercury porosimeter measured on the same sample for a pressure corresponding to 30 psi (approximately 0.2 MPa).

The volume of the macropores and of the mesopores is measured by porosimetry by intrusion of mercury according to standard ASTM D4284-83 at a maximum pressure of 4000 bar (400 MPa), using a surface tension of 484 dyne/cm and a contact angle of 140°. The value from which the mercury fills all the intergranular voids is set at 0.2 MPa and it is considered that, above this, the mercury penetrates into the pores of the sample.

The macropore volume of the catalyst or of the support used for the preparation of the catalyst according to the invention is defined as being the cumulative volume of mercury introduced at a pressure of between 0.2 MPa and 30 MPa, corresponding to the volume present in the pores with an apparent diameter of greater than 50 nm.

The mesopore volume of the catalyst or of the support used for the preparation of the catalyst according to the invention is defined as being the cumulative volume of mercury introduced at a pressure of between 30 MPa and 400 MPa, corresponding to the volume present in the pores with an apparent diameter of between 2 and 50 nm.

The micropore volume is measured by nitrogen porosimetry. The quantitative analysis of the microporosity is performed using the "t" method (method of Lippens-De Boer, 1965), which corresponds to a transform of the starting adsorption isotherm, as described in the work "Adsorption by powders and porous solids. Principles, methodology and applications", written by F. Rouquérol, J. Rouquérol and K. Sing, Academic Press, 1999.

The median mesopore diameter is also defined as being the diameter such that all the pores, among the combined pores constituting the mesopore volume, with a size of less than this diameter constitute 50% of the total mesopore volume determined by intrusion with a mercury porosimeter.

The median macropore diameter is also defined as being the diameter such that all the pores, among the combined pores constituting the macropore volume, with a size of less than this diameter constitute 50% of the total macropore volume determined by intrusion with a mercury porosimeter.

"Size of the nickel particles" is understood to mean the diameter of the nickel crystallites in oxide form. The diameter of the nickel crystallites in oxide form is determined by X-ray diffraction, from the width of the diffraction line located at the angle $2\theta=43°$ (i.e. along the crystallographic direction [200]) using the Scherrer relationship. This method, used in X-ray diffraction on polycrystalline samples or powders, which links the full width at half maximum of the diffraction peaks to the size of the particles, is described in detail in the reference: Appl. Cryst. (1978), 11, 102-113, "Scherrer after sixty years: A survey and some new results in the determination of crystallite size", J. I. Langford and A. J. C. Wilson.

The content of nickel and copper is measured by X-ray fluorescence.

2. Description

Catalyst

The invention relates to a catalyst comprising nickel and copper, in a proportion of 1% to 50% by weight of nickel element relative to the total weight of the catalyst, in a proportion of 0.5% to 15% by weight of copper element relative to the total weight of the catalyst, and an alumina support, said catalyst being characterized in that:
- the mole ratio between the nickel and the copper is between 0.5 and 5 mol/mol, preferably between 0.7 and 4.5 mol/mol, more preferentially between 0.9 and 4 mol/mol;
- at least one portion of the nickel and the copper is in the form of a nickel-copper alloy, advantageously corresponding to the formula $Ni_xCu_y$ with x between 0.1 and 0.9 and y between 0.1 and 0.9;
- the nickel content included in the nickel-copper alloy is between 0.5% and 15% by weight of nickel element relative to the total weight of the catalyst, preferably between 1% and 12% by weight, and more preferentially between 1% and 10% by weight;
- the size of the nickel particles, measured in oxide form, in the catalyst is less than 7 nm, preferably less than 5 nm, more preferentially less than 4 nm, and even more preferentially less than 3 nm.

The nickel content in said catalyst according to the invention is advantageously between 1% to 50% by weight relative to the total weight of the catalyst, more preferentially between 2% and 40% by weight and even more preferentially between 3% and 35% by weight and even more preferentially 5% and 25% by weight relative to the total weight of the catalyst.

The copper content is between 0.5% and 15% by weight of copper element relative to the total weight of the catalyst, preferably between 0.5% and 12% by weight, preferably between 0.75% and 10% by weight, and even more preferentially between 1% and 9% by weight.

The nickel content in the nickel-copper alloy is advantageously between 0.5% and 15% by weight of nickel element relative to the total weight of the catalyst, preferably between 1% and 12% by weight, and more preferentially between 1% and 10% by weight.

The mole ratio between nickel and copper is between 0.5 and 5 mol/mol, preferably between 0.7 and 4.5 mol/mol, more preferentially between 0.9 and 4 mol/mol.

The active phase of the catalyst does not comprise a metal from Group VIB. In particular, it does not comprise molybdenum or tungsten.

Said catalyst is generally presented in any form known to those skilled in the art, for example in the form of beads (generally having a diameter of between 1 and 8 mm), of extrudates, of tablets or of hollow cylinders. Preferably, it consists of extrudates with a diameter generally of between 0.5 and 10 mm, preferably between 0.8 and 3.2 mm and very preferably between 1.0 and 2.5 mm and with a mean length of between 0.5 and 20 mm. The "mean diameter" of the extrudates is intended to mean the mean diameter of the circle circumscribed in the cross section of these extrudates. The catalyst can advantageously be presented in the form of cylindrical, multilobate, trilobate or quadrilobate extrudates. Preferably, its shape will be trilobate or quadrilobate. The shape of the lobes could be adjusted according to all the methods known from the prior art.

The specific surface area of the catalyst is generally greater than or equal to 30 m²/g, preferably greater than or equal to 50 m²/g, more preferentially between 60 m²/g and 500 m²/g, and even more preferentially between 70 m²/g and 400 m²/g.

The total pore volume of the catalyst is generally between 0.1 and 1.5 cm³/g, preferably between 0.35 and 1.2 cm³/g, and even more preferentially between 0.4 and 1.0 cm³/g, and even more preferentially between 0.45 and 0.9 cm³/g.

The catalyst advantageously has a macropore volume less than or equal to 0.6 ml/g, preferably less than or equal to 0.5 ml/g, more preferentially less than or equal to 0.4 ml/g, and even more preferentially less than or equal to 0.3 ml/g.

The mesopore volume of the catalyst is generally at least 0.10 ml/g, preferably at least 0.20 ml/g, preferably between 0.25 ml/g and 0.80 ml/g, more preferably between 0.30 and 0.65 ml/g.

The median mesopore diameter is advantageously between 3 nm and 25 nm, and preferably between 6 and 20 nm and particularly preferably between 8 and 18 nm.

The catalyst advantageously exhibits a median macropore diameter of between 50 and 1500 nm, preferably between 80 and 1000 nm and more preferably still of between 250 and 800 nm.

Preferably, the catalyst exhibits a low microporosity; very preferably, it does not exhibit any microporosity.

Support

According to the invention, the support is an alumina, that is to say that the support comprises at least 95%, preferably at least 98%, and particularly preferably at least 99% by weight of alumina relative to the weight of the support. The alumina generally has a crystallographic structure of delta, gamma or theta alumina type, alone or as a mixture.

According to the invention, the alumina support may comprise impurities such as oxides of metals from groups IIA, IIIB, IVB, IIB, IIIA, IVA according to the CAS classification, preferably silica, titanium dioxide, zirconium dioxide, zinc oxide, magnesium oxide and calcium oxide, or else alkali metals, preferably lithium, sodium or potassium, and/or alkaline-earth metals, preferably magnesium, calcium, strontium or barium or else sulfur.

The specific surface area of the support is generally greater than or equal to 30 m²/g, preferably greater than or equal to 50 m²/g, more preferentially between 60 m²/g and 500 m²/g, and even more preferentially between 70 m²/g and 400 m²/g. The BET specific surface area is measured by nitrogen physisorption.

The total pore volume of the support is generally between 0.1 and 1.5 cm³/g, preferably between 0.35 and 1.2 cm³/g, and even more preferentially between 0.4 and 1.0 cm³/g, and even more preferentially between 0.45 and 0.9 cm³/g.

Process for Preparing the Catalyst

A subject of the present invention is a process for preparing a catalyst according to the invention, said process comprising the following steps:
- a) the alumina support is brought into contact with at least one solution containing at least one nickel precursor;
- b) the alumina support is brought into contact with at least one solution containing at least one nickel precursor and at least one copper precursor;
- c) the alumina support is brought into contact with at least one solution containing at least one organic compound comprising at least one carboxylic acid function, or at least one alcohol function, or at least one ester function, or at least one amide function, or at least one amine function, it being understood that:
- steps a), b) and c) are carried out separately, in any order, or
- steps a) and c) are carried out at the same time, step b) being carried out either before the combination of steps a) and c), or afterwards;
- steps b) and c) are carried out at the same time, step a) being carried out either before the combination of steps b) and c), or afterwards;
- d) at least one step of drying the catalyst precursor obtained at the end of steps a) to c) is carried out at a temperature below 250° C.;
- e) a step of reducing the catalyst precursor obtained at the end of step d) is carried out by bringing said precursor into contact with a reducing gas at a temperature above or equal to 150° C. and below 250° C.

The steps of the process for preparing the catalyst are explained in detail below.

Step a)—Bringing the Support into Contact with a Nickel Precursor

The deposition of nickel on said support, in accordance with the implementation of step a), can be carried out by dry impregnation or excess impregnation, or else by deposition-precipitation, according to methods well known to those skilled in the art.

Said step i) is preferentially carried out by impregnation of the support consisting, for example, in bringing said support into contact with at least one solution, which is aqueous or organic (for example methanol or ethanol or phenol or acetone or toluene or dimethyl sulfoxide (DMSO)) or else consists of a mixture of water and of at least one organic solvent, containing at least one nickel precursor at least partially in the dissolved state, or else in bringing said support into contact with at least one colloidal solution of at least one precursor of the nickel, in the oxidized form (nanoparticles of oxide, of oxy(hydroxide) or of hydroxide of the nickel) or in the reduced form (metal nanoparticles of the nickel in the reduced state). Preferably, the solution is aqueous. The pH of this solution could be modified by the optional addition of an acid or of a base. According to another preferred variant, the aqueous solution may contain ammonia or ammonium $NH_4^+$ ions.

Preferably, said step a) is carried out by dry impregnation, which consists in bringing the support of the catalyst into contact with a solution, containing at least one nickel precursor, the volume of the solution of which is between 0.25 and 1.5 times the pore volume of the support to be impregnated.

When the nickel precursor is introduced in aqueous solution, use is advantageously made of a nickel precursor in the nitrate, carbonate, acetate, chloride, hydroxide, hydroxycarbonate, oxalate, sulfate or formate form, in the form of complexes formed by a polyacid or an acid alcohol and its salts, in the form of complexes formed with acetylacetonates, in the form of tetrammine or hexammine complexes, or else in the form of any other inorganic derivative soluble in aqueous solution, which is brought into contact with said support.

Preferably, nickel nitrate, nickel hydroxide, nickel carbonate, nickel chloride or nickel hydroxycarbonate is advantageously used as nickel precursor. Very preferably, the nickel precursor is nickel nitrate, nickel carbonate or nickel hydroxide.

The amounts of the nickel precursor(s) introduced into the solution are chosen so that the total content of nickel is between 1% to 50% by weight, preferably between 2% and 40% by weight, preferably between 3% and 35% by weight of said element relative to the total weight of the catalyst, and more preferentially still between 5% and 25% by weight. In the embodiment in which step a) is carried out by dry impregnation or excess impregnation, preferably dry impregnation, the impregnation of the nickel with the support may advantageously be carried out via at least two impregnation cycles, using identical or different nickel precursors in each cycle. In this case, each impregnation is advantageously followed by drying and optionally by a heat treatment.

Step b) Bringing the Support into Contact with a Precursor of Copper and a Precursor of Nickel The deposition of nickel and copper on the alumina support may be carried out by dry impregnation or excess impregnation, or also by deposition-precipitation, according to methods well known to those skilled in the art.

Said step b) is preferentially carried out by impregnation of the catalyst precursor consisting for example in bringing said support into contact with at least one solution, which is aqueous or organic (for example methanol or ethanol or phenol or acetone or toluene or dimethyl sulfoxide (DMSO)) or else consists of a mixture of water and at least one organic solvent, comprising, preferably consisting of, at least one nickel precursor and at least one copper precursor at least partially in the dissolved state, or else in bringing said catalyst precursor into contact with at least one colloidal solution comprising, preferably consisting of, at least one nickel precursor and one copper precursor in oxidized form (nanoparticles of oxide, of oxy(hydroxide) or of hydroxide of nickel and copper) or in reduced form (metallic nanoparticles of nickel and copper in the reduced state). Preferably, the solution is aqueous. The pH of this solution may be modified by the optional addition of an acid or of a base.

Preferably, said step b) is carried out by dry impregnation, which consists in bringing the support of the catalyst precursor into contact with a solution comprising, preferably consisting of, at least one nickel precursor and at least one copper precursor, the volume of the solution of which is between 0.25 and 1.5 times the pore volume of the support to be impregnated.

When the nickel precursor is introduced in aqueous solution, use is advantageously made of a nickel precursor in the nitrate, carbonate, acetate, chloride, hydroxide, hydroxycarbonate, oxalate, sulfate or formate form, in the form of complexes formed by a polyacid or an acid alcohol and its salts, in the form of complexes formed with acetylacetonates, in the form of tetrammine or hexammine complexes, or else in the form of any other inorganic derivative soluble in aqueous solution, which is brought into contact with said catalyst precursor. Preferably, nickel nitrate, nickel hydroxide, nickel carbonate, nickel chloride or nickel hydroxycarbonate is advantageously used as nickel precursor. Very preferably, the nickel precursor is nickel nitrate, nickel carbonate or nickel hydroxide.

When the copper precursor is introduced in aqueous solution, a copper precursor in mineral or organic form is advantageously used. In mineral form, the copper precursor can be chosen from copper acetate, copper acetylacetonate, copper nitrate, copper sulfate, copper chloride, copper bromide, copper iodide or copper fluoride. Very preferably, the copper precursor salt is copper nitrate.

According to the invention, the nickel precursor is supplied in step b) at a desired concentration in order to obtain on the final catalyst (i.e. obtained at the end of the reduction step e) or the passivation step f) if the latter is carried out) a content of between 0.5% and 10% by weight of nickel element relative to the total weight of the final catalyst, preferably between 0.5% and 8% by weight, more preferentially between 1% and 7% by weight, even more preferentially between 1% and 5% by weight.

The amounts of the copper precursor(s) introduced into the solution according to step b) are chosen such that the total copper content is between 0.5% and 15% by weight of copper element relative to the total weight of the final catalyst (i.e. obtained at the end of the reduction step e) or the passivation step f) if the latter is carried out), preferably between 0.5% and 12% by weight, preferably between 0.75% and 10% by weight, and even more preferentially between 1% and 9% by weight.

Step c) Bringing the Support into Contact with an Organic Compound

Said support may be bought into contact with at least one solution containing at least one organic compound comprising at least one carboxylic acid function, or at least one alcohol function, or at least one ester function, or at least one amide function, or at least one amine function in accordance with the implementation of said step c), by any method well known to those skilled in the art. This is because it has in addition been noticed that the catalysts according to the invention prepared in the presence of an organic compound (mentioned above) are more active than the catalysts prepared in the absence of this type of organic compound. This effect is related to the decrease in the size of the nickel particles.

In particular, said step c) may be carried out by dry impregnation or by excess impregnation according to methods well known to those skilled in the art. Preferably, said step c) is carried out by dry impregnation, which consists in bringing the support of the catalyst into contact with a volume of said solution of between 0.25 and 1.5 times the pore volume of the support to be impregnated.

Said solution containing at least one organic compound comprising at least one carboxylic acid function, or at least one alcohol function, or at least one ester function, or at least one amide function, or at least one amine function, may be aqueous or organic (for example methanol or ethanol or phenol or acetone or toluene or dimethyl sulfoxide (DMSO)) or else consist of a mixture of water and of at least one organic solvent. Said organic compound is, beforehand, at least partially dissolved in said solution at the desired concentration. Preferably, said solution is aqueous or contains ethanol. More preferably still, said solution is aqueous. The pH of said solution could be modified by the optional addition of an acid or of a base. In another possible embodiment, the solvent may be absent from the impregnation solution.

In the embodiment in which step c) is carried out by dry impregnation or excess impregnation, preferably dry impregnation, the impregnation of the support with at least one solution containing at least said organic compound may advantageously be carried out via at least two impregnation cycles, using identical or different organic compounds in each cycle. In this case, each impregnation is advantageously followed by drying and optionally a heat treatment.

Advantageously, the mole ratio of said organic compound introduced in step c) to the nickel element also introduced in step a) is between 0.01 and 5.0 mol/mol, preferably between 0.05 and 2.0 mol/mol, more preferentially between 0.1 and 1.5 mol/mol and more preferentially still between 0.3 and 1.2 mol/mol.

The organic compound according to step c) may comprise, within the same molecule, several, identical or different, carboxylic acid, alcohol, ester, amide or amine organic functions. The organic compound according to step c) may comprise a combination of several organic functions chosen from carboxylic acid, alcohol, ester, amide or amine organic functions.

A) Organic Compound Comprising at least One Carboxylic Acid Function

In one embodiment according to the invention, the organic compound comprises at least one carboxylic acid function.

Said organic compound comprising at least one carboxylic acid function may be a saturated or unsaturated aliphatic organic compound or an aromatic organic compound. Preferably, the saturated or unsaturated aliphatic organic compound comprises between 1 and 9 carbon atoms, preferably between 2 and 7 carbon atoms. Preferably, the aromatic organic compound comprises between 7 and 10 carbon atoms, preferably between 7 and 9 carbon atoms.

Said saturated or unsaturated aliphatic organic compound or said aromatic organic compound comprising at least one carboxylic acid function may be chosen from monocarboxylic acids, dicarboxylic acids, tricarboxylic acids or tetracarboxylic acids. Advantageously, the organic compound comprising at least one carboxylic acid function is chosen from ethanedioic acid (oxalic acid), propanedioic acid (malonic acid), pentanedioic acid (glutaric acid), hydroxyacetic acid (glycolic acid), 2-hydroxypropanoic acid (lactic acid), 2-hydroxypropanedioic acid (tartronic acid), 2-hydroxypropane-1,2,3-tricarboxylic acid (citric acid), 2,3-dihydroxybutanedioic acid (tartaric acid), 2-oxopropanoic acid (pyruvic acid) or 4-oxopentanoic acid (levulinic acid).

B) Organic Compound Comprising at least One Alcohol Function

In another embodiment according to the invention, the organic compound comprises at least one alcohol function.

Preferably, said organic compound comprises between 2 and 20 carbon atoms, preferably between 2 and 12 carbon atoms and more preferably still between 2 and 8 carbon atoms.

Advantageously, the organic compound is chosen from methanol, ethanol, phenol, ethylene glycol, propane-1,3-diol, butane-1,4-diol, pentane-1,5-diol, hexane-1,6-diol, glycerol, xylitol, mannitol, sorbitol, pyrocatechol, resorcinol, hydroquinone, diethylene glycol, triethylene glycol, polyethylene glycols having an average molar mass of less than 600 g/mol, glucose, mannose, fructose, sucrose, maltose or lactose, in any one of the isomeric forms thereof.

C) Organic Compound Comprising at least One Ester Function

In another embodiment according to the invention, the organic compound comprises at least one ester function. Preferably, said organic compound comprises between 2 and 20 carbon atoms, preferably between 3 and 14 carbon atoms and more preferentially still between 3 and 8 carbon atoms.

Said organic compound may be chosen from a linear or cyclic or unsaturated cyclic carboxylic acid ester, or a cyclic or linear carbonic acid ester, or else a linear carbonic acid diester. In the case of a carboxylic acid cyclic ester, said compound is γ-valerolactone.

In the case of a carboxylic acid unsaturated cyclic ester (containing unsaturations in the ring), the compound can be furan or pyrone or any one of their derivatives, such as 6-pentyl-α-pyrone.

In the case of a carboxylic acid linear ester, the compound may be a compound comprising a single ester function corresponding to the empirical formula RCOOR', in which R and R' are linear, branched or cyclic alkyl groups, or alkyl groups containing unsaturations, or alkyl groups substituted by one or more aromatic rings, or aryl groups, each containing between 1 and 15 carbon atoms and which may be identical or different. The R group can also be the hydrogen atom H. Said organic compound is preferably methyl laurate.

In another embodiment according to the invention, the organic compound may be a compound comprising at least two carboxylic acid ester functions. Preferably, said compound is dimethyl succinate.

In another embodiment according to the invention, the organic compound may be a compound comprising at least one carboxylic acid ester function and at least one second functional group chosen from alcohols, ethers, ketones or aldehydes.

Preferably, said compound is dimethyl malate.

Advantageously, said organic compound comprises at least one carboxylic acid ester function and at least one ketone or aldehyde function. In the case of a carbonic acid cyclic ester, the compound is propylene carbonate. In the case of a carbonic acid linear ester, the compound is chosen from dimethyl carbonate, diethyl carbonate or diphenyl carbonate. In the case of a carbonic acid linear diester, the compound is chosen from dimethyl dicarbonate, diethyl dicarbonate or di(tert-butyl) dicarbonate.

D) Organic Compound Comprising at least One Amide Function

In another embodiment according to the invention, the organic compound comprises at least one amide function chosen from an acyclic amide function or a cyclic amide function optionally comprising alkyl substituents, aryl substituents or alkyl substituents containing unsaturations. The amide functions can be chosen from primary, secondary or tertiary Advantageously, the organic compound comprising at least one amide function is chosen from formamide, N-methylformamide, N,N-dimethylformamide, N-ethylformamide, N,N-diethylformamide, acetamide, N-methylacetamide, N,N-dimethylmethanamide, N,N-diethylacetamide, N,N-dimethylpropionamide, propanamide, 2-pyrrolidone, N-methyl-2-pyrrolidone, γ-lactam, caprolactam, acetylleucine, N-acetylaspartic acid, aminohippuric acid, N-acetylglutamic acid, 4-acetamidobenzoic acid, lactamide and glycolamide, urea, N-methylurea, N,N'-dimethylurea, 1,1-dimethylurea, and tetramethylurea, in any one of the isomeric forms thereof.

E) Organic Compound Comprising at Least One Amine Function

In another embodiment according to the invention, the organic compound comprises at least one amine function. Said organic compound comprises between 1 and 20 carbon atoms, preferably between 1 and 14 carbon atoms and more preferably still between 2 and 8 carbon atoms.

In one embodiment according to the invention, said organic compound comprising at least one amine function corresponding to the empirical formula $C_xN_yH_z$ in which $1 \leq x \leq 20$, $1 \leq y \leq x$, $2 \leq z \leq 2x+2$. More particularly, the organic compound is chosen from ethylenediamine, diaminohexane, tetramthylenediamine, hexamethylenediamine, tetramethylethylene-diamine, tetraethylethylenediamine, diethylenetriamine and triethylenetetramine.

In one embodiment according to the invention, said organic compound comprises at least one amine function and at least one carboxylic acid function (amino acid). When the compound is an amino acid, it is preferably chosen from alanine, arginine, lysine, proline, serine, threonine or EDTA.

Among all the above embodiments, the organic compound is chosen from oxalic acid, malonic acid, glycolic acid, lactic acid, tartronic acid, citric acid, tartaric acid, pyruvic acid, levulinic acid, ethylene glycol, propane-1,3- diol, butane-1,4-diol, glycerol, xylitol, mannitol, sorbitol, diethylene glycol, glucose, gamma-valerolactone, dimethyl carbonate, diethyl carbonate, formamide, N-methylformamide, acetamide, N-methylacetamide, N,N-dimethylmethanamide, 2-pyrrolidone, γ-lactam, lactamide, urea, alanine, arginine, lysine, proline, serine, EDTA.

Implementation of Steps a), b) and c)

According to the invention:
steps a), b) and c) are carried out separately, in any order, or
steps a) and c) are carried out at the same time, step b) being carried out either before the combination of steps a) and c), or afterwards;
steps b) and c) are carried out at the same time, step a) being carried out either before the combination of steps b) and c), or afterwards.

In one preferential embodiment, step a) is carried out before carrying out steps b) and c) at the same time.

In another preferential embodiment, steps a) and c) are carried out at the same time, and then step b) is carried out.

Step d) Drying the Impregnated Support

Step d) of drying the impregnated support is carried out at a temperature of less than 250° C., preferably of between 15° C. and 180° C., more preferentially between 30° C. and 160° C., even more preferentially between 50° C. and 150° C., and even more preferentially between 70° C. and 140° C., for a period typically of between 10 minutes and 24 hours. Longer periods of time are not ruled out, but do not necessarily provide any improvement.

The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air or nitrogen.

Heat Treatment of the Dried Catalyst (Optional Step)

The dried catalyst precursor can undergo an additional heat treatment step, before the reduction step e), at a temperature of between 250° C. and 1000° C. and preferably between 250° C. and 750° C., for a period typically between 15 minutes and 10 hours, under an inert atmosphere or under an oxygen-containing atmosphere, optionally in the presence of water. Longer treatment times are not ruled out but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed. After this or these treatment(s), the catalyst precursor comprises nickel in the oxide form, that is to say in the NiO form.

In the event of water being present, the water content is preferably between 150 and 900 grams per kilogram of dry air and even more preferably between 250 and 650 grams per kilogram of dry air.

Step e) Reduction with a Reducing Gas

Prior to the use of the catalyst in the catalytic reactor and the implementation of a hydrogenation process, a reducing treatment step e) is carried out in the presence of a reducing gas so as to obtain a catalyst comprising nickel at least partially in the metallic form. This step is advantageously carried out in situ, that is to say after charging of the catalyst to a reactor for hydrogenation of aromatic or polyaromatic compounds. This treatment makes it possible to activate said catalyst and to form metal particles, in particular of nickel in the zero-valent state. The in situ implementation of the catalyst reducing treatment makes it possible to dispense with an additional step of passivation of the catalyst with an oxygen-bearing compound or $CO_2$, which is necessarily the case when the catalyst is prepared by carrying out a reducing treatment ex situ, that is to say outside the reactor used for the hydrogenation of aromatic or polyaromatic compounds. In fact, when the reducing treatment is carried out ex situ, it is necessary to carry out a passivation step in order to preserve the metallic phase of the catalyst in the presence of air (during operations of transport and charging of the catalyst to the hydrogenation reactor), then to carry out a new step of reducing the catalyst.

The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one essential aspect of the preparation process according to the invention, said reducing treatment is carried out at a temperature above or equal to 150° C. and below 250° C., preferably between 160° C. and 230° C., and more preferentially between 170° C. and 220° C. The duration of the reducing treatment is between 5 minutes and less than 5 hours, preferably between 10 minutes and 4 hours, and even more preferentially between 10 minutes and 110 minutes.

The presence of the nickel-copper alloy at least partially in reduced form makes it possible to use operating conditions for reducing the nickel active phase which are less severe than in the prior art and thus makes it possible to carry out the reduction step directly within the reactor in which it is desired to carry out the hydrogenation of aromatic or polyaromatic compounds.

Furthermore, the presence of copper in the catalyst makes it possible to preserve good activity of the catalyst and a good service life of the catalyst when the latter is placed in contact with a hydrocarbon feedstock comprising sulfur. Indeed, compared to nickel, the copper present in the catalyst more easily captures the sulfur-containing compounds included in the feedstock, which limits the irreversible poisoning of the active sites. The rise in temperature up to the desired reduction temperature is generally slow, for example set between 0.1 and 10° C./min, preferably between 0.3 and 7° C./min.

The hydrogen flow rate, expressed in l/hour/gram of catalyst precursor, is between 0.01 and 100 l/hour/gram of catalyst, preferably between 0.05 and 10 l/hour/gram of catalyst precursor and more preferably still between 0.1 and 5 l/hour/gram of catalyst precursor.

Step f) Passivation (Optional)

The catalyst prepared according to the process according to the invention can undergo a passivation step with a sulfur-containing compound which makes it possible to improve the selectivity of the catalysts and to avoid thermal runaway during the start-up of new catalysts. The passivation generally consists in irreversibly poisoning, by the sulfur-containing compound, the most virulent active sites of the nickel which exist on the new catalyst and thus in weakening the activity of the catalyst in favor of its selectivity. The passivation step is carried out using methods known to those skilled in the art.

The passivation step with a sulfur-containing compound is generally carried out at a temperature of between 20° C. and 350° C., preferably between 40° C. and 200° C., for 10 to 240 minutes. The sulfur-containing compound is, for example, chosen from the following compounds: thiophene, thiophane, alkyl monosulfides, such as dimethyl sulfide, diethyl sulfide, dipropyl sulfide and propyl methyl sulfide, or also an organic disulfide of formula HO—$R_1$—S—S—$R_2$—OH, such as dithiodiethanol of formula HO—$C_2H_4$—S—S—$C_2H_4$—OH (often referred to as DEODS). The sulfur content is generally between 0.1% and 2% by weight of said element relative to the total weight of the catalyst.

In one embodiment according to the invention, the preparation of the catalyst is carried out ex situ, that is to say before loading the catalyst into the reaction unit of the process for selective hydrogenation or hydrogenation of aromatics.

Selective Hydrogenation Process

The catalyst obtained according to the process according to the invention can be used in a process for the selective hydrogenation of polyunsaturated compounds containing at least 2 carbon atoms per molecule, such as diolefins and/or acetylenics and/or alkenylaromatics, also known as styrenics, contained in a hydrocarbon feedstock having a final boiling point below or equal to 300° C. The process can be carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity of between 0.1 and 200 $h^{-1}$ when the process is carried out in the liquid phase, or at a hydrogen/(polyunsaturated compounds to be hydrogenated) mole ratio of between 0.5 and 1000 and at an hourly space velocity of between 100 and 40 000 $h^{-1}$ when the process is carried out in the gas phase, in the presence of the catalyst obtained by the preparation process as described above in the description.

Monounsaturated organic compounds, such as, for example, ethylene and propylene, are at the root of the manufacture of polymers, of plastics and of other chemicals having added value. These compounds are obtained from natural gas, from naphtha or from gas oil which have been treated by steam cracking or catalytic cracking processes. These processes are carried out at high temperature and produce, in addition to the desired monounsaturated compounds, polyunsaturated organic compounds, such as acetylene, propadiene and methylacetylene (or propyne), 1,2-butadiene and 1,3-butadiene, vinylacetylene and ethylacetylene, and other polyunsaturated compounds, the boiling point of which corresponds to the C5+ fraction (hydrocarbon-based compounds having at least 5 carbon atoms), in particular diolefinic or styrene or indene compounds. These polyunsaturated compounds are highly reactive and result in side reactions in the polymerization units. It is thus necessary to remove them before making economic use of these fractions.

Selective hydrogenation is the main treatment developed to specifically remove undesirable polyunsaturated compounds from these hydrocarbon feedstocks. It makes possible the conversion of polyunsaturated compounds to the corresponding alkenes or aromatics while avoiding their complete saturation and thus the formation of the corresponding alkanes or naphthenes. In the case of steam cracking gasolines used as feedstock, the selective hydrogenation also makes it possible to selectively hydrogenate the alkenylaromatics to give aromatics while avoiding the hydrogenation of the aromatic rings.

The hydrocarbon feedstock treated in the selective hydrogenation process has a final boiling point of below or equal to 300° C. and contains at least 2 carbon atoms per molecule and comprises at least one polyunsaturated compound. The term "polyunsaturated compounds" is intended to mean compounds comprising at least one acetylenic function and/or at least one diene function and/or at least one alkenylaromatic function.

More particularly, the feedstock is selected from the group consisting of a steam cracking C2 fraction, a steam cracking C2-C3 fraction, a steam cracking C3 fraction, a steam cracking C4 fraction, a steam cracking C5 fraction and a steam cracking gasoline, also known as pyrolysis gasoline or C5+ fraction.

The steam cracking C2 fraction, advantageously used for the implementation of the selective hydrogenation process, exhibits, for example, the following composition: between 40% and 95% by weight of ethylene and of the order of 0.1% to 5% by weight of acetylene, the remainder being essentially ethane and methane. In some steam cracking C2 fractions, between 0.1% and 1% by weight of C3 compounds may also be present.

The steam cracking C3 fraction, advantageously used for the implementation of the selective hydrogenation process, exhibits, for example, the following mean composition: of the order of 90% by weight of propylene and of the order of 1% to 8% by weight of propadiene and of methylacetylene, the remainder being essentially propane. In some C3 fractions, between 0.1% and 2% by weight of C2 compounds and of C4 compounds may also be present.

A C2-C3 fraction can also advantageously be used for the implementation of the selective hydrogenation process. It exhibits, for example, the following composition: of the order of 0.1% to 5% by weight of acetylene, of the order of 0.1% to 3% by weight of propadiene and of methylacetylene, of the order of 30% by weight of ethylene and of the order of 5% by weight of propylene, the remainder being essentially methane, ethane and propane. This feedstock may also contain between 0.1% and 2% by weight of C4 compounds.

The steam cracking C4 fraction, advantageously used for the implementation of the selective hydrogenation process, exhibits, for example, the following mean composition by weight: 1% by weight of butane, 46.5% by weight of butene, 51% by weight of butadiene, 1.3% by weight of vinylacetylene and 0.2% by weight of butyne. In some C4 fractions, between 0.1% and 2% by weight of C3 compounds and of C5 compounds may also be present.

The steam cracking C5 fraction, advantageously used for the implementation of the selective hydrogenation process, exhibits, for example, the following composition: 21% by weight of pentanes, 45% by weight of pentenes and 34% by weight of pentadienes.

The steam cracking gasoline or pyrolysis gasoline, advantageously used for the implementation of the selective hydrogenation process, corresponds to a hydrocarbon fraction, the boiling point of which is generally between 0 and 300° C., preferably between 10 and 250° C. The polyunsaturated hydrocarbons to be hydrogenated present in said steam cracking gasoline are in particular diolefin compounds (butadiene, isoprene, cyclopentadiene, and the like), styrene compounds (styrene, α-methylstyrene, and the like) and indene compounds (indene, and the like). The steam cracking gasoline generally comprises the C5-C12 fraction with traces of C3, C4, C13, C14 and C15 (for example between 0.1% and 3% by weight for each of these fractions). For example, a feedstock formed of pyrolysis gasoline generally has a composition as follows: 5% to 30% by weight of saturated compounds (paraffins and naphthenes), 40% to 80% by weight of aromatic compounds, 5% to 20% by weight of mono-olefins, 5% to 40% by weight of diolefins and 1% to 20% by weight of alkenylaromatic compounds, the combined compounds forming 100%. It also contains from 0 to 1000 ppm by weight of sulfur, preferably from 0 to 500 ppm by weight of sulfur.

Preferably, the polyunsaturated hydrocarbon feedstock treated in accordance with the selective hydrogenation process is a steam cracking C2 fraction or a steam cracking C2-C3 fraction or a steam cracking gasoline.

The selective hydrogenation process is targeted at removing said polyunsaturated hydrocarbons present in said feedstock to be hydrogenated without hydrogenating the mono-unsaturated hydrocarbons. For example, when said feedstock is a C2 fraction, the selective hydrogenation process is targeted at selectively hydrogenating acetylene. When said feedstock is a C3 fraction, the selective hydrogenation process is targeted at selectively hydrogenating propadiene and methylacetylene. In the case of a C4 fraction, the aim is to remove butadiene, vinylacetylene (VAC) and butyne; in the case of a C5 fraction, the aim is to remove the pentadienes. When said feedstock is a steam cracking gasoline, the selective hydrogenation process is targeted at selectively hydrogenating said polyunsaturated hydrocarbons present in said feedstock to be treated so that the diolefin compounds are partially hydrogenated to give mono-olefins and so that the styrene and indene compounds are partially hydrogenated to give corresponding aromatic compounds while avoiding the hydrogenation of the aromatic rings.

The technological implementation of the selective hydrogenation process is, for example, carried out by injection, as upflow or downflow, of the polyunsaturated hydrocarbon feedstock and of the hydrogen into at least one fixed bed reactor. Said reactor may be of isothermal type or of adiabatic type. An adiabatic reactor is preferred. The polyunsaturated hydrocarbon feedstock can advantageously be diluted by one or more reinjection(s) of the effluent, resulting from said reactor where the selective hydrogenation reaction takes place, at various points of the reactor, located between the inlet and the outlet of the reactor, in order to limit the temperature gradient in the reactor. The technological implementation of the selective hydrogenation process can also advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The selective hydrogenation of the steam cracking C2, C2-C3, C3, C4, C5 and C5+ fractions can be carried out in the gas phase or in the liquid phase, preferably in the liquid phase for the C3, C4, C5 and C5+ fractions and in the gas phase for the C2 and C2-C3 fractions. A liquid-phase reaction makes it possible to lower the energy cost and to increase the cycle period of the catalyst.

Generally, the selective hydrogenation of a hydrocarbon feedstock containing polyunsaturated compounds containing at least 2 carbon atoms per molecule and having a final boiling point below or equal to 300° C. is carried out at a temperature of between 0° C. and 300° C., at a pressure of between 0.1 and 10 MPa, at a hydrogen/(polyunsaturated compounds to be hydrogenated) mole ratio of between 0.1 and 10 and at an hourly space velocity HSV (defined as the ratio of the flow rate by volume of feedstock to the volume of the catalyst) of between 0.1 and 200 $h^{-1}$ for a process carried out in the liquid phase, or at a hydrogen/(polyunsaturated compounds to be hydrogenated) mole ratio of between 0.5 and 1000 and at an hourly space velocity HSV of between 100 and 40 000 $h^{-1}$ for a process carried out in the gas phase.

In one embodiment, when a selective hydrogenation process is carried out wherein the feedstock is a steam cracking gasoline comprising polyunsaturated compounds, the (hydrogen)/(polyunsaturated compounds to be hydrogenated) mole ratio is generally between 0.5 and 10, preferably between 0.7 and 5.0 and more preferably still between 1.0 and 2.0, the temperature is between 0° C. and 200° C., preferably between 20° C. and 200° C. and more preferably still between 30° C. and 180° C., the hourly space velocity (HSV) is generally between 0.5 and 100 $h^{-1}$, preferably between 1 and 50 $h^{-1}$, and the pressure is generally between 0.3 and 8.0 MPa, preferably between 1.0 and 7.0 MPa and more preferably still between 1.5 and 4.0 MPa.

More preferentially, a selective hydrogenation process is carried out wherein the feedstock is a steam cracking gasoline comprising polyunsaturated compounds, the hydrogen/(polyunsaturated compounds to be hydrogenated) mole ratio is between 0.7 and 5.0, the temperature is between 20° C. and 200° C., the hourly space velocity (HSV) is generally between 1 and 50 $h^{-1}$ and the pressure is between 1.0 and 7.0 MPa.

More preferentially still, a selective hydrogenation process is carried out wherein the feedstock is a steam cracking gasoline comprising polyunsaturated compounds, the hydrogen/(polyunsaturated compounds to be hydrogenated) mole ratio is between 1.0 and 2.0, the temperature is between 30° C. and 180° C., the hourly space velocity (HSV) is generally between 1 and 50 $h^{-1}$ and the pressure is between 1.5 and 4.0 MPa.

The hydrogen flow rate is adjusted in order to have available a sufficient amount thereof to theoretically hydrogenate all of the polyunsaturated compounds and to maintain an excess of hydrogen at the reactor outlet.

In another embodiment, when a selective hydrogenation process is carried out wherein the feedstock is a steam cracking C2 fraction and/or a steam cracking C2-C3 fraction comprising polyunsaturated compounds, the (hydrogen)/(polyunsaturated compounds to be hydrogenated) mole ratio is generally between 0.5 and 1000, preferably between 0.7 and 800, the temperature is between 0° C. and 300° C., preferably between 15° C. and 280° C., the hourly space velocity (HSV) is generally between 100 and 40 000 $h^{-1}$, preferably between 500 and 30 000 $h^{-1}$, and the pressure is generally between 0.1 and 6.0 MPa, preferably between 0.2 and 5.0 MPa.

Aromatics Hydrogenation Process

The catalyst obtained according to the process according to the invention can be used in a process for the hydrogenation of at least one aromatic or polyaromatic compound contained in a hydrocarbon feedstock having a final boiling point below or equal to 650° C., generally between 20° C. and 650° C., and preferably between 20° C. and 450° C. Said hydrocarbon feedstock containing at least one aromatic or polyaromatic compound can be chosen from the following petroleum or petrochemical fractions: the reformate from catalytic reforming, kerosene, light gas oil, heavy gas oil, cracking distillates, such as FCC recycle oil, coking unit gas oil or hydrocracking distillates.

The content of aromatic or polyaromatic compounds contained in the hydrocarbon feedstock treated in the hydrogenation process is generally between 0.1 and 80% by weight, preferably between 1 to 50% by weight, and particularly preferably between 2 and 35% by weight, the percentage being based on the total weight of the hydrocarbon feedstock. The aromatic compounds present in said hydrocarbon feedstock are, for example, benzene or alkylaromatics, such as toluene, ethylbenzene, o-xylene, m-xylene or p-xylene, or also aromatics having several aromatic rings (polyaromatics), such as naphthalene.

The sulfur or chlorine content of the feedstock is generally less than 5000 ppm by weight of sulfur or chlorine, preferably less than 100 ppm by weight, and particularly preferably less than 10 ppm by weight.

The technological implementation of the process for the hydrogenation of aromatic or polyaromatic compounds is, for example, carried out by injection, as upflow or downflow, of the hydrocarbon feedstock and of the hydrogen into at least one fixed bed reactor. Said reactor may be of isothermal type or of adiabatic type. An adiabatic reactor is preferred. The hydrocarbon feedstock may advantageously be diluted by one or more reinjection(s) of the effluent, resulting from said reactor where the reaction for the hydrogenation of the aromatics takes place, at various points of the reactor, located between the inlet and the outlet of the reactor, in order to limit the temperature gradient in the reactor. The technological implementation of the process for the hydrogenation of the aromatics may also advantageously be carried out by the implantation of at least said supported catalyst in a reactive distillation column or in reactors-exchangers or in a slurry-type reactor. The stream of hydrogen may be introduced at the same time as the feedstock to be hydrogenated and/or at one or more different points of the reactor.

The hydrogenation of the aromatic or polyaromatic compounds may be carried out in the gas phase or in the liquid phase, preferably in the liquid phase. Generally, the hydrogenation of the aromatic or polyaromatic compounds is carried out at a temperature of between 30° C. and 350° C., preferably between 50° C. and 325° C., at a pressure of between 0.1 and 20 MPa, preferably between 0.5 and 10 MPa, at a hydrogen/(aromatic compounds to be hydrogenated) mole ratio between 0.1 and 10 and at an hourly space velocity HSV of between 0.05 and 50 $h^{-1}$, preferably between 0.1 and 10 $h^{-1}$, of a hydrocarbon feedstock containing aromatic or polyaromatic compounds and having a final boiling point below or equal to 650° C., generally between 20° C. and 650° C., and preferably between 20° C. and 450° C.

The hydrogen flow rate is adjusted in order to have available a sufficient amount thereof to theoretically hydrogenate all of the aromatic compounds and to maintain an excess of hydrogen at the reactor outlet.

The conversion of the aromatic or polyaromatic compounds is generally greater than 20 mol %, preferably greater than 40 mol %, more preferably greater than 80 mol %, and particularly preferably greater than 90 mol % of the aromatic or polyaromatic compounds contained in the hydrocarbon feedstock. The conversion is calculated by dividing the difference between the total moles of the aromatic or polyaromatic compounds in the hydrocarbon feedstock and in the product by the total moles of the aromatic or polyaromatic compounds in the hydrocarbon feedstock.

According to a specific alternative form of the process, a process for the hydrogenation of the benzene of a hydrocarbon feedstock, such as the reformate resulting from a catalytic reforming unit, is carried out. The benzene content in said hydrocarbon feedstock is generally between 0.1 and 40% by weight, preferably between 0.5 and 35% by weight, and particularly preferably between 2 and 30% by weight, the percentage by weight being based on the total weight of the hydrocarbon feedstock.

The sulfur or chlorine content of the feedstock is generally less than 10 ppm by weight of sulfur or chlorine respectively, and preferably less than 2 ppm by weight.

The hydrogenation of the benzene contained in the hydrocarbon feedstock may be carried out in the gas phase or in the liquid phase, preferably in the liquid phase. When it is carried out in the liquid phase, a solvent may be present, such as cyclohexane, heptane or octane. Generally, the hydrogenation of the benzene is carried out at a temperature of between 30° C. and 250° C., preferably between 50° C. and 200° C., and more preferably between 80° C. and 180° C., at a pressure of between 0.1 and 10 MPa, preferably between 0.5 and 4 MPa, at a hydrogen/(benzene) mole ratio between 0.1 and 10 and at an hourly space velocity HSV of between 0.05 and 50 $h^{-1}$, preferably between 0.5 and 10 $h^{-1}$.

The conversion of the benzene is generally greater than 50 mol %, preferably greater than 80 mol %, more preferably greater than 90 mol % and particularly preferably greater than 98 mol %.

The invention will now be illustrated by the following examples which are in no way limiting.

EXAMPLES

For all of the catalysts mentioned in the examples mentioned below, the support is an alumina A having a specific surface area of 80 $m^2/g$, a pore volume of 0.7 ml/g and a median pore diameter of 12 nm.

Example 1: Preparation of an Aqueous Solution of Ni Precursors

The aqueous solution of Ni precursors (solution S1) used for the preparation of the catalyst A is prepared by dissolving 43.5 g of nickel nitrate ($NiNO_3$, supplier Strem Chemicals®) in a volume of 13 ml of distilled water. The solution S1, the Ni concentration of which is 350 g of Ni per liter of solution, is obtained.

Example 2: Preparation of an Aqueous Solution of Ni Precursors with Additives The aqueous solution of Ni precursors (solution S2) used for the preparation of the catalysts B to G is prepared by dissolving 43.5 g of nickel nitrate ($NiNO_3$, supplier Strem Chemicals®) and malonic acid (CAS 141-82-2; supplier Fluka®) in a volume of 13 ml of distilled water. The additive/Ni mole ratio being 0.5. The solution S2, the Ni concentration of which is 350 g of Ni per liter of solution, is obtained.

Example 3: Preparation of an Aqueous Solution of the Precursors of the NiCu Alloy (5% Ni)

The aqueous solution of Ni precursors (solution S3) used for the preparation of the catalysts C, D, E, and G is prepared by dissolving 14.5 g of nickel nitrate ($NiNO_3$, supplier Strem Chemicals®) in a volume of 13 ml of distilled water. A solution, the Ni concentration of which is 116.6 g of Ni per liter of solution, is obtained. The copper nitrate precursor is then added in order to have in particular an Ni/Cu mole ratio of 1 (catalysts C to F) and 2 (catalyst G) according to the examples. The solution S3 is obtained. It makes it possible to introduce the precursors of the NiCu alloy with a weight content of Ni relative to the final catalyst of about 5 wt %.

This solution is adapted to obtain an alloy containing 2 wt % of Ni relative to the final catalyst (catalyst F).

Example 4: Catalyst A (Not in Accordance with the Invention)

The solution S prepared in example 1 is dry impregnated on 10 g of alumina A. The solid thus obtained is subsequently dried in an oven overnight at 120° C. and then calcined under a stream of dry air of 1 l/h/g of catalyst at 450° C. for 2 hours. The calcined catalyst thus prepared contains 15% by weight of nickel element relative to the total weight of the catalyst supported on alumina.

The dry air used in this example and in all the examples below contains less than 5 grams of water per kilogram of air.

The catalyst precursor is then reduced under the conditions as described in example 11 below.

Example 5: Catalyst B (Not in Accordance with the Invention)

The solution S2 prepared in example 2 is dry impregnated on 10 g of alumina A. The solid thus obtained is subsequently dried in an oven overnight at 120° C., and then calcined under a stream of air of 1 l/h/g of catalyst at 450° C. for 2 hours. The calcined catalyst thus prepared contains 15% by weight of nickel element relative to the total weight of the catalyst supported on alumina.

The catalyst precursor is then reduced under the conditions as described in example 11 below.

Example 6: Catalyst C (Not in Accordance with the Invention)

The solution S2 and the solution S3 prepared in examples 2 and 3 are co-impregnated on 10 g of the alumina A. The solid thus obtained is subsequently dried in an oven overnight at 120° C., and then calcined under a stream of air of 1 l/h/g of catalyst at 450° C. for 2 hours. The catalyst precursor is then reduced under the conditions as described in example 11 below.

Example 7: Catalyst D (In Accordance with the Invention)

The solution S2 is dry impregnated on alumina A to obtain 15% of Ni alone relative to the total weight of the final catalyst. The solid thus obtained is subsequently dried in an oven overnight at 120° C., and then calcined under a stream of air of 1 l/h/g of catalyst at 450° C. for 2 hours. Next, the solution S3 (with a targeted Ni/Cu mole ratio=3) is dry impregnated on the catalyst precursor. The targeted Ni content in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 11 below.

Example 8: Catalyst E (In Accordance with the Invention)

The solution S3 (with a targeted Ni/Cu ratio=3) is dry impregnated on alumina A. The targeted Ni content in this step is 5% by weight of Ni relative to the weight of the final catalyst. The solid thus obtained is subsequently dried in an oven overnight at 120° C., and then calcined under a stream of air of 1 l/h/g of catalyst at 450° C. for 2 hours. The solution S2 is then dry impregnated on the catalyst precursor to obtain 15% of Ni alone relative to the total weight of the final catalyst. The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 11 below.

Example 9: Catalyst F (In Accordance with the Invention)

The solution S2 is dry impregnated on alumina A to obtain 15% of Ni alone relative to the total weight of the final catalyst. The solid thus obtained is subsequently dried in an oven overnight at 120° C., and then calcined under a stream of air of 1 l/h/g of catalyst at 450° C. for 2 hours. The solution S3 prepared and adapted in example 3 is dry impregnated on the catalyst precursor. The targeted Ni content in this step is 2% by weight of Ni relative to the weight of the final catalyst. The targeted Ni/Cu ratio is 3. The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 11 below.

Example 10: Catalyst G (In Accordance with the Invention)

The solution S2 is dry impregnated on alumina A to obtain 15% of Ni alone relative to the total weight of the final catalyst. The solid thus obtained is subsequently dried in an oven overnight at 120° C., and then calcined under a stream of air of 1 l/h/g of catalyst at 450° C. for 2 hours. The solution S3 prepared in example 3 is dry impregnated on the catalyst precursor. The targeted Ni content in this step is 2% by weight of Ni relative to the weight of the final catalyst. The targeted Ni/Cu ratio is 1. The solid thus obtained is subsequently dried in an oven overnight at 120° C., and then calcined under a stream of air of 1 l/h/g of catalyst at 450° C. for 2 hours.

The catalyst precursor is then reduced under the conditions as described in example 11 below.

Example 11: Characterization

All the catalysts contain the contents targeted during impregnation, that is to say 15% of nickel element (characterized by X-ray fluorescence) relative to the total weight of the catalyst, and the % of copper added (characterized by X-ray fluorescence).

The amount of alloy obtained after the calcining then reduction step was determined by X-ray diffraction (XRD) analysis on samples of catalyst in powder form.

The amount of nickel in metallic form obtained after the reduction step was determined by X-ray diffraction (XRD) analysis on samples of catalyst in powder form. Between the reduction step and throughout the duration of the characterization by XRD, the catalysts are never returned to the open air. The diffraction patterns are obtained by radiocrystallographic analysis by means of a diffractometer using the conventional powder method with K$\alpha$1 radiation of copper ($\lambda$=1.5406 Å).

The degree of reduction was calculated by calculating the area of the line of Ni° located around 52° 2θ, on all of the diffractograms of each sample of catalyst analyzed, then by subtracting the signal present as soon as ambient temperature is reached under the line at 52°, which is due to alumina.

Table 1 below collates the degrees of reduction or else the content of nickel metal Ni° (expressed as % by weight relative to the total weight of active nickel, i.e. the nickel that does not make up the alloy) for all the catalysts A to G characterized by XRD after a reduction step at 170° C. for 90 minutes under a hydrogen stream. These values were also compared with the degree of reduction obtained for catalyst A (Ni alone) after a conventional reduction step (that is to say at a temperature of 400° C. for 15 hours under a hydrogen stream).

Alumina in delta and theta form and large CuO and NiO lines are detected at ambient temperature on all the copper- and nickel-containing catalysts, after calcination.

A line corresponding to the alloy in $Ni_{0.76}Cu_{0.24}$ form is moreover detected after reduction.

In order to evaluate the degree of reducibility and therefore the formation of Ni°, the area of the line of Ni° located around 52° 2θ is measured, on all the diffractograms, by subtracting the signal present as soon as ambient temperature is reached under the line at 52°, which is due to the alumina. It is thus possible to determine the relative percentage of Ni° crystallized after reduction.

Table 1 below summarizes the degrees of reducibility or the Ni° content for all the catalysts characterized by XRD after reduction at 170° C. for 90 minutes under a hydrogen stream. These values were also compared with the degree of reduction obtained for catalyst A (Ni alone) after a conventional reduction step (that is to say at a temperature of 400° C. for 15 hours under a hydrogen stream).

(catalyst G) with an Ni content of 2% (catalyst F) or 5% (catalyst D, E, G) also enables a reduction of the nickel oxide to Ni° of the order of 90% in the end on the catalyst.

Example 12: Catalytic Test: Performance in Selective Hydrogenation of a Mixture Containing Styrene and Isoprene ($A_{HYD1}$)

Catalysts A to G described in the above examples are tested with regard to the reaction for the selective hydrogenation of a mixture containing styrene and isoprene.

The composition of the feedstock to be selectively hydrogenated is as follows: 8% by weight of styrene (supplied by Sigma Aldrich®, purity 99%), 8% by weight of isoprene (supplied by Sigma Aldrich®, purity 99%) and 84% by weight of n-heptane (solvent) (supplied by VWR®, purity>99% Chromanorm HPLC). This composition corresponds to the initial composition of the reaction mixture. This mixture of model molecules is representative of a pyrolysis gasoline.

The selective hydrogenation reaction is carried out in a 500 ml stainless steel autoclave which is provided with a magnetically-driven mechanical stirrer and which is able to operate under a maximum pressure of 100 bar (10 MPa) and temperatures of between 5° C. and 200° C.

214 ml of n-heptane (supplied by VWR®, purity>99% Chromanorm HPLC) and an amount of 3 ml of catalyst are added to an autoclave. The autoclave is closed and purged. The autoclave is then pressurized under 35 bar (3.5 MPa) of hydrogen. The catalyst is first reduced in situ, at 170° C. for 90 minutes under a hydrogen stream of 1 l/h/g (temperature rise gradient of 1° C./min) for catalysts A to G (which corresponds here to step e) of the preparation process according to the invention according to one embodiment).

TABLE 1

| Catalyst | Final reduction | Ni content for the 1st imp. (wt %) | Ni content for the 2nd imp. (wt %) | Ni/Cu mole ratio | Size of the particles (nm) | Percentage of Ni° alone (XRD) after reduction (%) |
|---|---|---|---|---|---|---|
| A (comparative) | 400° C., 15 h | 15 | — | — | 14 | 80 |
| A (comparative) | 170° C., 90 min | 15 | — | — | 14 | 0* |
| B (comparative) | 170° C., 90 min | 15 | — | — | 2 | 0* |
| C (comparative) | 170° C., 90 min | A single impregnation S2 + S3 | | 3 | 10 | 0** |
| D (invention) | 170° C., 90 min | 15 | 5 | 3 | 2 | 90 |
| E (invention) | 170° C., 90 min | 5 | 15 | 3 | 2 | 95 |
| F (invention) | 170° C., 90 min | 15 | 2 | 3 | 2 | 90 |
| G (invention) | 170° C., 90 min | 15 | 5 | 1 | 2 | 95 |

*Nickel in the form of NiO
**Nickel in alloy form

For catalyst A (15% Ni alone/alumina), the degree of nickel reducibility is 0% after exactly the same reduction treatment under hydrogen as for catalysts B to E. It is necessary to reduce at 400° C. in order to have a reduction of the nickel oxide to Ni° of the order of 80%.

Catalyst C prepared by co-impregnation of solutions S2 and S3 has according to the XRD only NiCu alloy and no active phase of Ni° alone.

The nickel post-impregnation or pre-impregnation of solution S3 with an Ni/Cu ratio of 3 (catalysts D, E, F) or 1

The autoclave is then brought to the test temperature, equal to 30° C. At time t=0, approximately 30 g of a mixture containing styrene, isoprene, n-heptane, pentanethiol and thiophene are introduced into the autoclave. The reaction mixture then has the composition described above and stirring is started at 1600 rpm. The pressure is kept constant at 35 bar (3.5 MPa) in the autoclave using a storage cylinder located upstream of the reactor.

Another test was carried out for catalyst A, but with a catalyst reduction temperature of 400° C. for 15 hours.

The progress of the reaction is monitored by taking samples from the reaction medium at regular time intervals: the styrene is hydrogenated to give ethylbenzene, without hydrogenation of the aromatic ring, and the isoprene is hydrogenated to give methylbutenes. If the reaction is prolonged for longer than necessary, the methylbutenes are in their turn hydrogenated to give isopentane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to G are reported in table 2 below. They are related to the catalytic activity ($A_{HYD1}$) measured for catalyst A prepared under conventional reduction conditions (at a temperature of 400° C. for 15 hours under a hydrogen stream).

Example 13: Catalytic Tests: Performance in Hydrogenation of Toluene ($A_{HYD2}$)

Catalysts A to G described in the above examples are also tested with regard to the reaction for the hydrogenation of toluene.

The selective hydrogenation reaction is carried out in the same autoclave as that described in Example 10.

214 ml of n-heptane (supplied by VWR®, purity>99% Chromanorm HPLC) and an amount of 3 ml of catalyst are added to an autoclave. The autoclave is closed and purged. The autoclave is then pressurized under 35 bar (3.5 MPa) of hydrogen. The catalyst is first reduced in situ, at 170° C. for 90 minutes under a hydrogen stream of 1 l/h/g (temperature rise gradient of 1° C./min) for catalysts A to G (which corresponds here to step e) of the preparation process according to the invention according to one embodiment). After addition of 216 ml of n-heptane (supplied by VWR®, purity>99% Chromanorm HPLC), the autoclave is closed, purged, then pressurized under 35 bar (3.5 MPa) of hydrogen and brought to the test temperature, equal to 80° C. At time t=0, approximately 26 g of toluene (supplied by SDS®, purity>99.8%) are introduced into the autoclave (the initial composition of the reaction mixture is then 6 wt % toluene/ 94 wt % n-heptane) and stirring is started at 1600 rpm. The pressure is kept constant at 35 bar (3.5 MPa) in the autoclave using a storage cylinder located upstream of the reactor.

The progress of the reaction is monitored by taking samples from the reaction medium at regular time intervals: the toluene is completely hydrogenated to give methylcyclohexane. The hydrogen consumption is also monitored over time by the decrease in pressure in a storage cylinder located upstream of the reactor. The catalytic activity is expressed in moles of $H_2$ consumed per minute and per gram of Ni.

The catalytic activities measured for catalysts A to G are reported in table 2 below. They are related back to the catalytic activity ($A_{HYD2}$) measured for catalyst A prepared under conventional reduction conditions (at a temperature of 400° C. for 15 hours under a hydrogen stream in an ex situ continuous-flow reactor).

TABLE 2

| Catalyst | Final reduction | Size of the Ni° particles (nm) | Percentage of Ni° alone (XRD) after reduction (%) | $A_{HYD1}$ (%) | $A_{HYD2}$ (%) |
|---|---|---|---|---|---|
| A (comparative) | 400° C., 15 h | 14 | 80 | 100 | 100 |
| A (comparative) | 170° C., 90 min | 14 | 0* | <1 | <1 |
| B (comparative) | 170° C., 90 min | 2 | 0* | <1 | <1 |
| C (comparative) | 170° C., 90 min | — | 0** | 15 | 20 |
| D (invention) | 170° C., 90 min | 2 | 90 | 185 | 190 |
| E (invention) | 170° C., 90 min | 2 | 95 | 175 | 185 |
| F (invention) | 170° C., 90 min | 2 | 90 | 172 | 182 |
| G (invention) | 170° C., 90 min | 2 | 95 | 180 | 192 |

*Nickel in the form of NiO
**Nickel in alloy form

Catalysts A and B reduced at 170° C. for 90 minutes are not active owing to their reduced Ni content of 0. On the other hand, if the temperature is increased to 400° C., catalyst A is active owing to its reduced Ni content of the order of 80%. However, the 14 nm particle size gives it a relatively modest catalytic activity. Catalyst C does not have according to the XRD reduced Ni alone, the activity evaluated in examples 11 and 12 is due to the presence of the alloy which has a slightly hydrogenating character, but much less so than the reduced Ni alone (a much lower activity compared to the reference (of the order of 20%)).

This clearly shows the improved performance of catalysts D to G according to the invention, compared to the catalyst of Ni alone on alumina reduced at 170° C. for 90 min, which is completely inactive. Furthermore, the small particles obtained owing to the use of solution 2 enable a substantial gain in activity even compared to catalyst A reduced at 400° C.

The invention claimed is:

1. A process for preparing a catalyst, said catalyst comprising nickel and copper in a proportion of 1% to 50% by weight of nickel element relative to the total weight of the catalyst and in a proportion of 0.5% to 15% by weight of copper element relative to the total weight of the catalyst, and an alumina support, wherein in said catalyst:
   the mole ratio between nickel and copper is between 0.5 and 5 mol/mol;
   at least one portion of the nickel and copper is in the form of a nickel-copper alloy;
   the nickel content in the nickel-copper is between 0.5% and 15% by weight of nickel element relative to the total weight of the catalyst,
   the size of the nickel particles in the catalyst, measured in oxide form, is less than 7 nm,
   said method comprising the following steps:
   a) bringing the alumina support into contact with at least one solution containing at least one nickel precursor;
   b) bringing the alumina support into contact with at least one solution containing at least one nickel precursor and at least one copper precursor;
   c) bringing the alumina support into contact with at least one solution containing at least one organic compound comprising at least one carboxylic acid function, or at least one alcohol function, or at least one ester function, or at least one amide function, or at least one amine function, wherein:
- steps a), b) and c) are carried out separately, in any order, or
- steps a) and c) are carried out at the same time, step b) being carried out either before the combination of steps a) and c), or afterwards;
- steps b) and c) are carried out at the same time, step a) being carried out either before the combination of steps b) and c), or afterwards;

d) carrying out at least one step of drying the catalyst precursor obtained at the end of steps a) to c) at a temperature below 250° C.;

e) carrying out a step of reducing the catalyst precursor obtained at the end of step d) by bringing said precursor into contact with a reducing gas at a temperature above or equal to 150° C. and below 250° C.

2. The process as claimed in claim 1, wherein, in the catalyst, the size of the nickel particles is less than 5 nm.

3. The process as claimed in claim 1, wherein, in the catalyst, the support is in the form of an extrudate with a mean diameter of between 0.5 and 10 mm.

4. The process as claimed in claim 3, wherein, in the catalyst, the support is in the form of a trilobate or quadrilobate extrudate.

5. The process as claimed in claim 1, wherein the mole ratio between said organic compound introduced in step c) and the nickel element also introduced in step a) is between 0.01 and 5.0 mol/mol.

6. The process as claimed in claim 1, wherein the organic compound of step c) is chosen from oxalic acid, malonic acid, glycolic acid, lactic acid, tartronic acid, citric acid, tartaric acid, pyruvic acid, levulinic acid, ethylene glycol, propane-1,3-diol, butane-1,4-diol, glycerol, xylitol, mannitol, sorbitol, diethylene glycol, glucose, gamma-valerolactone, dimethyl carbonate, diethyl carbonate, formamide, N-methylformamide, acetamide, N-methylacetamide, N,N-dimethylmethanamide, 2-pyrrolidone, γ-lactam, lactamide, urea, alanine, arginine, lysine, proline, serine, and EDTA.

7. The process as claimed in claim 1, wherein step e) is carried out at a temperature between 130° C. and 190° C.

8. The process as claimed in claim 1, wherein step e) is carried out for between 10 minutes and 110 minutes.

9. The process as claimed in claim 1, wherein the copper precursor is chosen from copper acetate, copper acetylacetonate, copper nitrate, copper sulfate, copper chloride, copper bromide, copper iodide and copper fluoride.

10. The process as claimed in claim 9, wherein the copper precursor is copper nitrate.

11. The process as claimed in claim 1, wherein steps a), b) and c) are carried out separately, in any order.

12. The process as claimed in claim 1, wherein in step c) the at least one organic compound is malonic acid.

13. The process as claimed in claim 1, wherein in step c) the at least one organic compound comprises at least one carboxylic acid function, or at least one ester function, or at least one amide function, or at least one amine function.

* * * * *